United States Patent [19]

Bodor et al.

[11] 3,957,803

[45] May 18, 1976

[54] CERTAIN TRANSIENT PRO-DRUG FORMS OF PHENYLBUTAZONE

[75] Inventors: Nicolae S. Bodor; Kenneth B. Sloan, both of Lawrence, Kans.

[73] Assignee: Interx Research Corporation, Lawrence, Kans.

[22] Filed: Jan. 6, 1975

[21] Appl. No.: 538,903

[52] U.S. Cl. .................. 260/295 L; 260/295.5 A; 260/310 A; 424/263; 424/273
[51] Int. Cl.² ..................................... C07D 213/81
[58] Field of Search ...... 260/310 A, 295 L, 295.5 A

[56] References Cited
OTHER PUBLICATIONS

Burger, Medicinal Chemistry, Third Edition, Part 2, Wiley–Interscience Pub. pp. 958–960, (1970).

*Primary Examiner*—Alan L. Rotman
*Attorney, Agent, or Firm*—Charles N. Blitzer

[57] ABSTRACT

Transient, pro-drug forms of phenylbutazone and oxyphenbutazone, which are 1,2-diphenyl-4-butyl-5-oxy-4-pyrazolin-3-one derivatives, are disclosed.

These compounds exhibit anti-inflammatory activity in warm-blooded animals. Upon administration to warm-blooded animals, these compounds pass through the gastrointestinal tract and "cleave" in the bloodstream, thus releasing phenylbutazone or oxyphenbutazone in an anti-inflammatory effective amount at their therapeutic site or sites of activity.

16 Claims, No Drawings

CERTAIN TRANSIENT PRO-DRUG FORMS OF PHENYLBUTAZONE

BACKGROUND OF THE INVENTION

1. Field of the Invention

The present invention is directed to novel, transient, pro-drugs useful as anti-inflammatory agents in warm-blooded animals (e.g., humans). More particularly, the present invention extends to certain novel, transient, pro-drug forms of phenylbutazone and oxyphenbutazone, known and proven anti-inflammatory agents.

For the purposes of this application, the term "pro-drug" denotes a derivative of a known and proven prior art compound (i.e., phenylbutazone and oxyphenbutazone) which derivative, when administered to a warm-blooded animal, "cleaves" in such a manner as to release the proven drug form and permit the same to attain a higher therapeutic level and/or reduced toxic action than that which could be attained if the proven drug form per se was administered.

The term "transient" denotes enzymatic and/or chemical hydrolytic "cleavage" of the compounds of this invention is such a manner that the proven drug form (phenylbutazone or oxyphenbutazone) is released and the remaining "cleaved" moiety remains nontoxic and metabolized in such a manner that nontoxic, metabolic products are produced.

2. Description of the Prior Art

Phenylbutazone and oxyphenbutazone represent non-hormonal anti-inflammatory agents, highly effective in the treatment of rheumatoid disorders and other non-specific inflammatory conditions. Chemically, phenylbutazone and oxyphenbutazone are 4-butyl-1,2-diphenyl-3,5-pyrazolidinedione and 4-butyl-2-(p-hydroxyphenyl)-1-phenyl-3,5-pyrazolidinedione, respectively.

The analgesic, antipyretic and anti-inflammatory actions of phenylbutazone and oxyphenbutazone are manifested as prompt relief of pain, lysis of fever and diminution of swelling, tenderness and local heat. The dosage regimen will vary with the size of the individual treated as well as the individual's needs. However, conventionally, an initial daily dose in adults ranges from 300 to 600 mg, divided into three or four equal doses.

While phenylbutazone and oxyphenbutazone are highly recognized anti-inflammatory agents, their respective solubilities cause extreme gastric irritation which is manifested by blood loss from the gastrointestinal (GI) tract. Essentially, phenylbutazone and oxyphenbutazone are relatively insoluble in the GI tract. In order to alleviate tis situation, numerous salts and complexes of these compounds have been prepared. However, these new derivatives revert back to phenylbutazone and oxyphenbutazone, respectively, extremely rapidly in the GI tract. As a result, phenylbutazone and oxyphenbutazone are released in the GI tract (not in the bloodstream), and because of their insolubility therein, (1) they are not readily absorbed into the bloodstream, and (2) extreme GI irritation is observed. In addition, compounds specifically related to those of formula (I) above have been prepared in the past (see, U.S. Pat. Nos. 2,905,694 and 3,607,881 and Spanish Pat. No. 379,995). However, these compounds are relatively insoluble as well, and, therefore, offer no advantage over the other prior art compounds. That is, these compounds, being relatively insoluble are not absorbed readily through the GI tract. Consequently, they will not readily release phenylbutazone in the bloodstream and will not minimize GI irritation.

SUMMARY OF THE INVENTION

It is, therefore, one object of the present invention to provide selected derivatives of phenylbutazone and oxyphenbutazone for administration to warm-blooded animals (e.g., humans) which will pass through the gastrointestinal tract and subsequently "cleave" upon absorption into the bloodstream to release phenylbutazone and oxyphenbutazone in an anti-inflammatory effective amount at their therapeutic site or sites of activity.

It is another object of the present invention to provide selected derivatives of phenylbutazone and oxyphenbutazone as above described which, in addition to passing through the GI tract, dramatically minimizes irritation therein.

It is still another object of the present invention to provide derivatives of phenylbutazone and oxyphenbutazone as previously described, wherein following "cleavage" of the pro-drug, thus releasing phenylbutazone or oxyphenbutazone at their therapeutic site or sites of activity, the pro-drug moiety (that which is not related to the parent compound) is metabolized in a nontoxic fashion.

All the foregoing objects are obtained with selected transient, pro-drug forms of phenylbutazone and oxyphenbutazone as provided below:

(I) 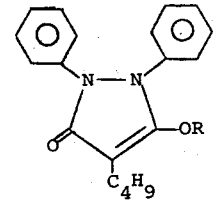

wherein R represents a member selected from the group consisting of a $C_1$–$C_2$ O-alkylsulfonyl group, an aryl(phenyl, p-tolyl, naphthyl)sulfonyl group, a nicotinoyl group, an iso-nicotinoyl group, a picolinoyl group, an N-protected naturally occurring amino acid residue, wherein the protective group on the amino group of the amine acid residue is removable via hydrogenolysis or hydrolysis, and an amino acid residue containing a $C_1$–$C_2$ N,N-dialkylamino or a $C_4$–$C_6$ cycloalkylamino group.

(II) 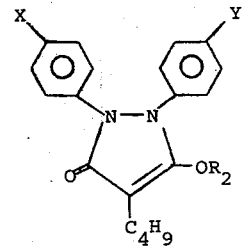

wherein X and Y each represent a member selected from the group consisting of a hydrogen atom and a —$OR_1$ group, with the proviso that either X or Y is a hydrogen atom and that $R_2$ is a member selected from the same or different groups represented by $R_1$; and wherein $R_1$ represents a member selected from the group consisting of a hydrogen atom, a $C_1-C_2$ O-alkylsulfonyl group, an aryl(phenyl, p-tolyl, naphthyl)sulfonyl group, a —$CH_2COOM$ group, wherein M represents an alkali or alkaline earth metal (Na, K, Ca, Mg); a —CO—$R_3$ group, wherein $R_3$ represents a member selected from the group consisting of a straight or branched $C_1-C_5$ alkyl group, a $C_1-C_2$ alkoxy group, a phenyl group, a substituted phenyl group whose substituents are selected from the group consisting of a 2,3, or 4-hydroxy group, a 2,3, or 4-acetyloxy group, and a 2,3, or 4-acetylamino group, a 2,3, or 4-pyridyl group, a 1,2, or 5-imidazolyl group, a residue of an N-protected naturally occurring amino acid, wherein the protective group on the amino group of the amino acid is removable via hydrogenolysis or hydrolysis, and an amino acid residue containing a $C_1-C_2$ N,N-dialkylamino or $C_4-C_5$ cycloalkylamino group.

(III)

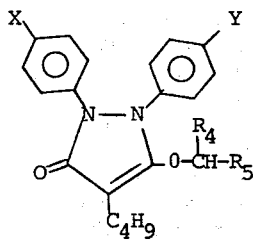

wherein X or Y represents a member selected from the group consisting of a hydrogen atom and a —$OR_1$ group, wherein $R_1$ is as defined above with the proviso that either X or Y is a hydrogen atom; wherein $R_4$ represents a member selected from the group consisting of a hydrogen atom, a $C_1-C_5$ alkyl group, an aryl group (phenyl, styryl), a 2,3, or 4-methoxyphenyl group, and a —$CH=CH_2$ group; and wherein $R_5$ represents a member selected from the group consisting of a —OOC—$R_6$ group, a

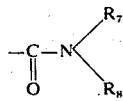

group, and a —COOM group, wherein M represents an alkali or alkaline earth metal (Na, K, Ca, Mg), wherein $R_6$ represents a member selected from the group consisting of $R_4$ as defined above, with the proviso that $R_6$ cannot be a hydrogen atom, and wherein $R_7$ and $R_8$ each represent a $C_1-C_3$ alkyl group.

With respect to the phrases "N-protected naturally occurring amino acid" and "amino acid residue" used above, any conventional amino acid disclosed in U.S. Pat. No. 3,803,120 — Felix, et al will suffice. Illustrative of N-protective groups are those described in "Synthetic Peptides", Vol. 1, p. 5 by George R. Pettit (1970) and "Chemistry of the Amino Acids", Vol. 2, p. vi by Jesse P. Greenstein and Milton Winitz (1961).

While the foregoing objects are met with all the compounds of formulas (I) through (III) above, nevertheless, certain selected compounds are preferred as set out below:

1. 1,2-Diphenyl-4-butyl-5-(3'-carboxypyridyl)-4-pyrazolin-3-one
2. 1,2-Diphenyl-4-butyl-5-(2'-carboxypyridyl)-4-pyrazolin-3-one
3. 1,2-Diphenyl-4-butyl-5-(4'-carboxypyridyl)-4-pyrazolin-3-one
4. 1,2-Diphenyl-4-butyl-5-pivalyloxy-4-pyrazolin-3-one
5. 1,2-Diphenyl-4-butyl-5-(N,N-dimethylcarbamoyloxy)-4-pyrazolin-3-one
6. 1,2-Diphenyl-4-butyl-5-(N,N-diethylcarbamoyloxy)-4-pyrazolin-3-one
7. 1,2-Diphenyl-4-butyl-5-(N-formylglycyloxy)-4-pyrazolin-3-one
8. 1,2-Diphenyl-4-butyl-5-(N-ethoxycarbonylglycyloxy)-4-pyrazolin-3-one
9. 1,2-Diphenyl-4-butyl-5-(N-benzyloxycarbonylglycyloxy)-4-pyrazolin-3-one
10. 1,2-Diphenyl-4-butyl-5-(4'-methylphenylsulfonyloxy)-4-pyrazolin-3-one
11. 1,2-Diphenyl-4-butyl-5-methylsulfonyloxy-4-pyrazolin-3-one
12. 1,2-Diphenyl-4-butyl-5-ethylsulfonyloxy-4-pyrazolin-3-one
13. 1,2-Diphenyl-4-butyl-5-camphorsulfonyloxy-4-pyrazolin-3-one
14. 1,2-Diphenyl-4-butyl-5-pivalyloxymethoxy-4-pyrazolin-3-one
15. 1,2-Diphenyl-4-butyl-5-benzoyloxymethoxy-4-pyrazolin-3-one
16. 1,2-Diphenyl-4-butyl-5-cinnamoyloxymethoxy-4-pyrazolin-3-one
17. 1,2-Diphenyl-4-butyl-5-benzoyloxybenzyloxy-4-pyrazolin-3-one
18. 1,2-Diphenyl-4-butyl-5-acetyloxymethoxy-4-pyrazolin-3-one
19. 1,2-Diphenyl-4-butyl-5-(N,N-dimethylcarbamoylmethoxy)-4-pyrazolin-3-one
20. 1,2-Diphenyl-4-butyl-5-(N,N-diethylcarbamoylmethoxy)-4-pyrazolin-3-one
21. 1-(4'-Acetyloxyphenyl)-2-phenyl-4-butyl-5-acetyloxy-4-pyrazolin-3-one
22. 1-(4'-Acetyloxyphenyl)-2-phenyl-4-butyl-5-(3'-carboxypyridyl)-4-pyrazolin-3-one
23. 1-(4'-Acetyloxyphenyl)-2-phenyl-4-butyl-5-(2'-carboxypyridyl)-4-pyrazolin-3-one
24. 1-(4'-Acetyloxyphenyl)-2-phenyl-4-butyl-5-(4'-carboxypyridyl)-4-pyrazolin-3-one
25. 1-(4'-Acetyloxyphenyl)-2-phenyl-4-butyl-5-pivalyloxy-4-pyrazolin-3-one
26. 1-(4'-Acetyloxyphenyl)-2-phenyl-4-butyl-5-(N,N-dimethylcarbamoyloxy)-4-pyrazolin-3-one
27. 1-(4'-Acetyloxyphenyl)-2-phenyl-4-butyl-5-(N,N-diethylcarbamoyloxy)-4-pyrazolin-3-one
28. 1-(4'-Acetyloxyphenyl)-2-phenyl-4-butyl-5-(N-formylglycyloxy)-4-pyrazolin-3-one
29. 1-(4'-Acetyloxyphenyl)-2-phenyl-4-butyl-5-(N-ethoxycarbonylglycyloxy)-4-pyrazolin-3-one
30. 1-(4'-Acetyloxyphenyl)-2-phenyl-4-butyl-5-(N-benzyloxycarbonyl-glycyloxy)-4-pyrazolin-3-one
31. 1-(4'-Acetyloxyphenyl)-2-phenyl-4-butyl-5-(4'-methylphenyl-sulfonyloxy)-4-pyrazolin-3-one
32. 1-(4'-Acetyloxyphenyl)-2-phenyl-4-butyl-5-methylsulfonyloxy-4-pyrazolin-3-one
33. 1-(4'-acetyloxyphenyl)-2-phenyl-4-butyl-5-ethylsulfonyloxy-4-pyrazolin-3-one
34. 1-(4'-Acetyloxyphenyl)-2-phenyl-4-butyl-5-camphorsulfonyloxy-4-pyrazolin-3-one
35. 1-(4'-Acetyloxyphenyl)-2-phenyl-4-butyl-5-pivalyloxymethoxy-4-pyrazolin-3-one 36. 1-(4'-Acetyloxyphenyl)-2-phenyl-4-butyl-5-benzoyloxymethoxy-4-pyrazolin-3-one
37. 1-(4'-Acetyloxyphenyl)-2-phenyl-4-butyl-5-cinnamoyloxymethoxy-4-pyrazolin-3-one
38. 1-(4'-Acetyloxyphenyl)-2-phenyl-4-butyl-5-benzoyloxybenzyloxy-4-pyrazolin-3-one
39. 1-(4'-Acetyloxyphenyl)-2-phenyl-4-butyl-5-acetyloxymethoxy-4-pyrazolin-3-one
40. 1-Phenyl-2-(4'-acetyloxyphenyl)-4-butyl-5-acetyloxy-4-pyrazolin-3-one
41. 1-Phenyl-2-(4'-acetyloxyphenyl)-4-butyl-5-(3'-carboxypyridyl)-4-pyrazolin-3-one
42. 1-Phenyl-2-(4'-acetyloxyphenyl)-4-butyl-5-(2'-carboxypyridyl)-4-pyrazolin-3-one
43. 1-Phenyl-2-(4'-acetyloxyphenyl)-4-butyl-5-(4'-carboxypyridyl)-4-pyrazolin-3-one
44. 1-Phenyl-2-(4'-acetyloxyphenyl)-4-butyl-5-pivalyloxy-4-pyrazolin-3-one
45. 1-Phenyl-2-(4'-acetyloxyphenyl)-4-butyl-5-(N,N-dimethylcarbamoyloxy)-4-pyrazolin-3-one
46. 1-Phenyl-2-(4'-acetyloxyphenyl)-4-butyl-5-(N,N-diethylcarbamoyloxy)-4-pyrazolin-3-one
47. 1-Phenyl-2-(4'-acetyloxyphenyl)-4-butyl-5-(N-formylglycyloxy)-4-pyrazolin-3-one
48. 1-Phenyl-2-(4'-acetyloxyphenyl)-4-butyl-5-(N-ethoxycarbonylglycyloxy)-4-pyrazolin-3-one
49. 1-Phenyl-2-(4'-acetyloxyphenyl)-4-butyl-5-(N-benzyloxycarbonylglycyloxy)-4-pyrazolin-3-one
50. 1-Phenyl-2-(4'-acetyloxyphenyl)-4-butyl-5-(4'-methylphenylsulfonyloxy)-4-pyrazolin-3-one
51. 1-Phenyl-2-(4'-acetyloxyphenyl)-4-butyl-5-methylsulfonyloxy-4-pyrazolin-3-one
52. 1-Phenyl-2-(4'-acetyloxyphenyl)-4-butyl-5-ethylsulfonyloxy-4-pyrazolin-3-one
53. 1-Phenyl-2-(4'-acetyloxyphenyl)-4-butyl-5-camphorsulfonyloxy-4-pyrazolin-3-one
54. 1-Phenyl-2-(4'-acetyloxyphenyl)-4-butyl-5-pivalyloxymethoxy-4-pyrazolin-3-one
55. 1-Phenyl-2-(4'-acetyloxyphenyl)-4-butyl-5-benzoyloxymethoxy-4-pyrazolin-3-one
56. 1-Phenyl-2-(4'-acetyloxyphenyl)-4-butyl-5-cinnamoyloxymethoxy-4-pyrazolin-3-one
57. 1-Phenyl-2-(4'-acetyloxyphenyl)-4-butyl-5-benzoyloxybenzyloxy-4-pyrazolin-3-one
58. 1-Phenyl-2-(4'-acetyloxyphenyl)-4-butyl-5-acetyloxymethoxy-4-pyrazolin-3-one
59. 1-(4'-Benzoyloxyphenyl)-2-phenyl-4-butyl-5-benzoyloxy-4-pyrazolin-3-one
60. 1-(4'-Benzoyloxyphenyl)-2-phenyl-4-butyl-5-acetyloxy-4-pyrazolin-3-one
61. 1-(4'-Benzoyloxyphenyl)-2-phenyl-4-butyl-5-(3'-carboxypyridyl)-4-pyrazolin-3-one
62. 1-(4'-Benzoyloxyphenyl)-2-phenyl-4-butyl-5-(2'-carboxypyridyl)-4-pyrazolin-3-one
63. 1-(4'-Benzoyloxyphenyl)-2-phenyl-4-butyl-5-(4'-carboxypyridyl)-4-pyrazolin-3-one
64. 1-(4'-Benzoyloxyphenyl)-2-phenyl-4-butyl-5-pivalyloxy-4-pyrazolin-3-one
65. 1-(4'-Benzoyloxyphenyl)-2-phenyl-4-butyl-5-(N,N-dimethylcarbamoyloxy)-4-pyrazolin-3-one
66. 1-(4'-Benzoyloxyphenyl)-2-phenyl-4-butyl-5-(N,N-diethylcarbamoyloxy)-4-pyrazolin-3-one
67. 1-(4'-Benzoyloxyphenyl)-2-phenyl-4-butyl-5-(N-formylglycyloxy)-4-pyrazolin-3-one
68. 1-(4'-Benzoyloxyphenyl)-2-phenyl-4-butyl-5-(N-ethoxycarbonylglycyloxy)-4-pyrazolin-3-one
69. 1-(4'-Benzoyloxyphenyl)-2-phenyl-4-butyl-5-(N-benzyloxycarbonylglycyloxy)-4-pyrazolin-3-one
70. 1-(4'-Benzoyloxyphenyl)-2-phenyl-4-butyl-5-(4'-methylphenylsulfonyloxy)-4-pyrazolin-3-one
71. 1-(4'-Benzoyloxyphenyl)-2-phenyl-4-butyl-5-methylsulfonyloxy-4-pyrazolin-3-one
72. 1-(4'-Benzoyloxyphenyl)-2-phenyl-4-butyl-5-ethylsulfonyloxy-4-pyrazolin-3-one
73. 1-(4'-Benzoyloxyphenyl)-2-phenyl-4-butyl-5-camphorsulfonyloxy-4-pyrazolin-3-one
74. 1-(4'-Benzoyloxyphenyl)-2-phenyl-4-butyl-5-pivalyloxymethoxy-4-pyrazolin-3-one
75. 1-(4'-Benzoyloxyphenyl)-2-phenyl-4-butyl-5-benzoyloxymethoxy-4-pyrazolin-3-one
76. 1-(4'-Benzoyloxyphenyl)-2-phenyl-4-butyl-5-cinnamoyloxymethoxy-4-pyrazolin-3-one
77. 1-(4'-Benzoyloxyphenyl)-2-phenyl-4-butyl-5-benzoyloxybenzyloxy-4-pyrazolin-3-one
78. 1-(4'-Benzoyloxyphenyl)-2-phenyl-4-butyl-5-acetyloxymethoxy-4-pyrazolin-3-one The compounds of the present invention are prepared in a convenient manner as outlined below.

PREPARATION OF THE COMPOUNDS OF FORMULA (I)

METHOD "A" (PREPARATION OF THOSE COMPOUNDS EXCLUSIVE OF THE SULFONATE DERIVATIVES)

First, phenylbutazone is dissolved in a slight excess of trifluoroacetic anhydride (TFAA) at room temperature and standard pressure for a period of 1 – 2 hours. Then, the resulting intermediate compound is treated with a slight excess of the acid anhydride of "R" in Formula (I). The excess acid is neutralized via extraction of a dichloromethane solution of the above reaction mixture with three equivalents of an aqueous inorganic base of an alkali or alkaline earth metal, such as KOH, NaOH, NaHCO$_3$. The final compound is isolated by evaporation of the dichloromethane and purification is conventionally carried out via recrystallization from a chloroform/heptane mixture or any conventional halogenated hydrocarbon solvent (e.g., chloroform, dichloromethane, etc.), or any equivalent solvent.

The process described herein under Method "A" is deemed novel by the present inventors, and as such, this particular process is included within the inventive scope of this invention. Moreover, the intermediate product derived from the reaction between phenylbutazone and trifluoroacetic anhydride (1,2-diphenyl-3,5-ditrifluoroacetyloxy-4-butyl-5-hydroxy-3-pyrazoline) is also deemed novel by the present inventors and is included within their invention as well.

METHOD "B" (PREPARATION OF THE SULFONATE DERIVATIVES)

A suitable salt of phenylbutazone (K, Na, triethylammonium, Tl (I), etc.) is reacted with the corresponding sulfonyl chloride in an inert organic solvent, such as ether, dimethylformamide, tetrahydrofuran (THF), benzene, etc. over a period of 1 to 24 hours, at room temperature and standard pressure. The halide salt is then filtered off or washed from the reaction mixture, and the final product is isolated following evaporation of the dried solvent. If necessary, the final product can be conventionally recrystallized.

PREPARATION OF THE COMPOUNDS OF FORMULA (II)

METHOD "A" (WHEN $R_1$ AND $R_2$ ARE IDENTICAL AND OTHER THAN —$CH_2COOM$)

Oxyphenbutazone is mixed with two equivalents of a conventional trialkylamine, such as triethylamine at room temperature and standard pressure, in the presence of a suitable solvent (e.g., a halogenated hydrocarbon, such as chloroform, or benzene). The resulting mixture is then treated with two equivalents of an appropriate acyl chloride (e.g., acetyl chloride, benzoyl chloride, or the like) at room temperature and standard pressure for a period of 1 to 24 hours. After washing with water and drying the solvent with sodium sulfate, the solvent is evaporated to give the final product. If necessary, the final product can be recrystallized by conventional procedures.

METHOD "B" (WHEN $R_1$ AND $R_2$ ARE NOT THE SAME AND OTHER THAN —$CH_2COOM$)

The $R_1$ moiety of Formula (II) is introduced by reacting oxyphenbutazone with an acyl chloride (e.g., acetyl chloride, benzoyl chloride, etc.) or an acyl anhydride in the presence of an acid catalyst such as p-toluenesulfonic acid, sulfosalicylic acid or the like in the presence of an inert organic solvent such as a carboxylic acid (e.g., acetic acid), ethyl acetate, toluene, benzene, etc. After neutralization of the catalyst, the final product is obtained via solvent evaporation. If necessary, conventional recrystallization of the final product can be carried out.

In the second step, the $R_2$ moiety of Formula (II) is introduced via the procedure of Method "A" of Formula (II) above, but using only one equivalent of triethylamine. In this step the use of only one equivalent of triethylamine is critical to the introduction of the $R_2$ moiety.

METHOD "C" (WHEN $R_1$ AND/OR $R_2$ EQUAL —$CH_2COOM$)

First, a suitable disalt of oxyphenbutazone (e.g., Na, K, Tl (I)) is reacted with chloroacetic acid at room temperature and standard pressure for a period of 1 to 24 hours in water or a suitable inert organic solvent, such as THF, acetone, or dichloromethane. After filtering off the organic halides, the final compound is isolated via solvent evaporation. The dicarboxylic acid formed can be converted to its M salt by simply adding two equivalents of an M—OH base in alcohol followed by solvent evaporation, wherein M represents an alkali or alkaline earth metal as described earlier.

THE COMPOUNDS OF FORMULA (III)

METHOD "A" (WHEN X AND Y ARE BOTH HYDROGEN)

A suitable salt of phenylbutazone (e.g., alkali or alkaline earth metal salt, Tl (I), or triethylammonium salt) is reacted in an inert organic solvent, such as acetone, dichloromethane, THF, etc. with a compound of the Formula:

wherein $R_4$ and $R_5$ are as defined above in Formula (III), and wherein X represents a halogen atom such as chlorine, bromine, or iodine. The reaction is carried out at standard pressure and at the reflux temperature of the solvent employed for a period of 1 to 24 hours. After filtering or washing off the halogen salt formed, the final product is isolated by evaporation of the solvent. If necessary, the final product may be recrystallized conventionally.

During this reaction, in many instances, in addition to obtaining the title compounds of Formula (III), a $C_4$ isomer of the title compounds having the following formula can also be obtained:

(IV) 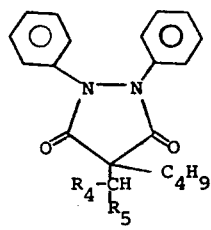

wherein $R_4$ and $R_5$ are as defined above.

METHOD "B" (WHEN X OR Y ARE NOT HYDROGEN)

The $R_1$ moiety as defined in Formula (III) is introduced per Method "B" described for the preparation of the compounds of Formula (II) above. The protected oxyphenbutazone thus obtained is then reacted with a compound of the formula:

as desscribed earlier in Method "A" of Formula (III) to obtain the final product.

In all the above reaction schemes for the preparation of the compounds of Formula (I) through (III) stoichiometric amounts of each reactant are employed unless otherwise indicated.

It should be noted that in those instances where transient derivatives of oxyphenbutazone of the Formula (II) and (III) are prepared, two isomers having the following formula can form:

ISOMERS FOR THE COMPOUNDS OF FORMULA (II)

(V) 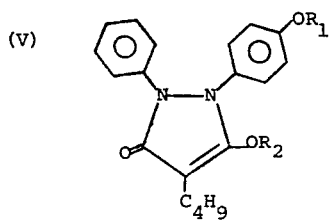   (VI) 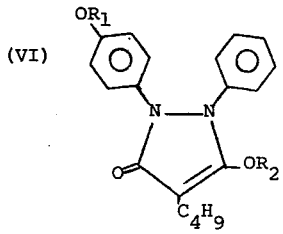

ISOMERS FOR THE COMPOUNDS OF FORMULA (III)

(VII) 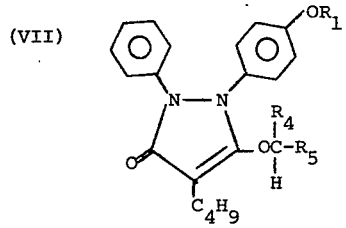   (VIII) 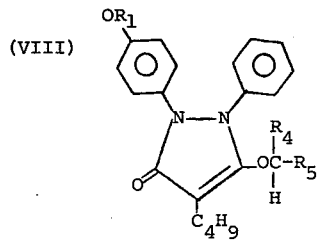

In the above formulas, $R_1$, $R_2$, $R_4$, and $R_5$ are defined as above.

No attempts were made to separate these isomers because a possible mixture of the isomers would serve the same purpose, ie., deliverying oxyphenbutazone in the manner described in this application.

Without further elaboration, it is believed that one skilled in the art can, using the preceding description, utilize the present invention to its fullest extent. The following preferred specific embodiments are, therefore, to be construed as merely illustrative, and not limitative of the remainder of the specification and claims in any way whatsoever. Unless otherwise indicated, all references to temperature denotes Centigrade.

EXAMPLE 1

1,2-DIPHENYL-4-BUTYL-5-(3'-CARBOXYPYRIDYL)-4-PYRAZOLIN-3-ONE

Phenylbutazone (1,2-diphenyl-3,5-pyrazolidinedione; 11.00 g, 0.035 mole) was treated with 11.55 g (0.055 mole) of trifluoroacetic anhydride. The resulting solid suspension was shaken or mechanically stirred until a homogeneous solution was obtained, then it was stirred with a magnetic stirrer at room temperature in a tightly closed flask for one hour. The solution was concentrated in vacuo for one hour and the oily residue obtained was dissolved in 50 ml of acetone and allowed to react with 12.5 g (0.055 mole) of nicotinic anhydride. The initial suspension became homogeneous after 0.25 hours with concomitant formation of a yellow color. After an additional one hour at room temperature, the yellow solution was concentrated in vacuo and the residue was dissolved in 200 ml of dichloromethane. The dichloromethane solution was extracted first with an aqueous sodium bicarbonate solution (12.2 g, 0.145 mole in 150 ml), then with an aqueous sodium hydroxide solution (28 g, 0.07 mole in 56 ml) and subsequently dried over sodium sulfate. The dichloromethane solution was concentrated in vacuo and the residue was crystallized from dichloromethane petroleum ether bp 30°–60° C to give 11.16 g (mp 139°–141° C, 77.5% yield) of the title compound.

Anal. Calcd for $C_{25}H_{23}N_3O_3$: C, 72.62; H, 5.61; N, 10.16. Found: C, 72.39; H, 5.64; N, 9.98.

EXAMPLE 2

1-(4'-BENZOYLOXYPHENYL)-2-PHENYL-4-BUTYL-5-BENZOYLOXY-4-PYRAZOLIN-3-ONE and

1-PHENYL-2-(4'-BENZOYLOXYPHENYL)-4-BUTYL-5-BENZOYLOXY-4-PYRAZOLIN-3-ONE

A dichloromethane (10 ml) solution containing 1.12 g (8.0 mmole) of benzoyl chloride was added to a dichloromethane (50 ml) solution containing 0.81 g (8.0 mmole) of triethylamine and 1.25 g (3.85 mmole) of oxyphenbutazone [1-phenyl-2-(4'hydroxyphenyl)-3,5-pyrazolidinedione]. The resulting solution warmed immediately, and after one hour at room temperature TLC (silica gel, ether) analysis of the reaction mixture showed that only one component could be observed. The solution was washed with water (100 ml) and the dichloromethane layer was separated, dried over sodium sulfate and concentrated in vacuo. The residue was crystallized from dichloromethane-heptane to give 1.81 g (88% yield) of a white solid which gave a wide melting point range due to the fact that it was a mixture of the title compounds.

Anal. Calcd for $C_{33}H_{28}N_2O_5$: C, 74.42; H, 5.29; N, 5.24. Found: C, 74.58; H, 5.41; N, 5.06.

EXAMPLE 3

1-PHENYL-2-(4'-ACETYLOXYPHENYL)-4-BUTYL-5-PIVALYLOXY-4-PYRAZOLIN-3-ONE and 1-(4'-ACETYLOXYPHENYL)-2-PHENYL-4-BUTYL-5-PIVALYLOXY-4-PYRAZOLIN-3-ONE First, 1-Phenyl-2-(4'-acetyloxyphenyl)-3,5-pyrazolidinedione was prepared as follows. Oxyphenbutazone (1.00 g, 3.1 mmole) was suspended in 4 ml of glacial acetic acid and allowed to react with 2 ml of acetyl chloride at room temperature overnight. The solution was concentrated in vacuo at 86° C to give a white residue (mp 126°–130° C). The residue was crystallized from chloroformheptane (6:50) with cooling to give 0.81 g (mp 132°–134° C, 71% yield, lit., R. Pfester and F. Hafliger, *Helvetica Chemica Acta*, 40, 395 (1957) mp 135°–137° C from methanol) of 1-phenyl-2-(4'-acetyloxyphenyl)-3,5-pyrazolidinedione.

Anal. Calcd for $C_{21}H_{22}N_2O_4$: C, 68.83; H, 6.05; N, 7.65. Found: C, 69.08; H, 6.01; N, 7.38.

Next, the Thallium (I) salt of 1-phenyl-2-(4'-acetyloxyphenyl)-3,5-pyrazolidinedione (acetyloxyphenbutazone; 0.77 g, 2.1 mmole) was partially suspended in 50 ml of dry ether into which there was added 0.52 g (2.1 mmole) of Thallium (I) ethoxide dissolved in 10 ml of dry ether. A precipitate formed immediately. The suspension was stirred at room temperature for 2 hours and then the suspension was filtered and the residue was dried to give 1.11 g (mp 170°–175° C (dec.), 93% yield) of the white solid Thallium (I) salt of acetyloxyphenbutazone. The Thallium (I) salt was resuspended in dry ether (50 ml) and 0.21 g (1.9 mmole) of pivalyl chloride dissolved in 10 ml of dry ether was added to the suspension. The suspension was stirred overnight at room temperature and then it was filtered and the filtrate concentrated in vacuo to give an oil. The oil was partially crystallized from dichloromethane-heptane-ether to give 0.15 g (mp 151°–158° C) of a white solid which was shown to contain three components upon analysis by TLC analysis. The major component was separated on a preparative TLC plate (silica gel, heptane-ether 1:1) to give the title compounds (mp 156°–158° C).

Anal. Calcd for $C_{26}H_{30}N_2O_5$: C, 69.31; H, 6.71; N, 6.22. Found: C, 69.03; H, 6.77; N, 6.11.

EXAMPLE 4

1,2-DIPHENYL-4-BUTYL-5-PIVALYLOXYMETHOXY-4-PYRAZOLIN-3-ONE and 1,2-DIPHENYL-4-BUTYL-4-PIVALYLOXYMETHYL-3,5-PYRAZOLIDINEDIONE Potassium carbonate (2.26 g, 0.016 mole) was suspended in an acetone (125 ml) solution of phenylbutazone and the suspension was refluxed overnight. The next day pivalyloxymethyl chloride (4.99 g, 0.033 mole) was added to the resulting solution and the solution was refluxed overnight. The suspension was cooled and filtered; the residue (2.00 g, 83%) was potassium chloride. The filtrate was concentrated in vacuo and the residue was suspended in ether, then filtered. The residue was washed with ether until the washings did not contain any product by TLC. The residue from the ether suspension was the potassium salt of phenylbutazone (2.25 g, 20%). The ether was then concentrated in vacuo and the residue was absorbed on silica gel and chromatographed on neutral silica gel (CC-7, Mallinckrodt) using petroleum ether bp 30°–60° C — ether (1:1) as the eluent to give two fractions. The first fraction (Rf 0.46, silica gel, heptane-ether, 1:1) was crystallized from heptane-petroleum ether bp 30°–60° C, 1:1 to give 0.63 g (mp 116°–117° C, 5% yield) of 1,2-diphenyl-4-butyl-4-pivalyloxymethyl-3,5-pyrazolidinedione. nmr (CDCl$_3$) δ 4.40

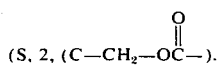

(S, 2, (C—CH$_2$—OC—).

Anal. Calcd for $C_{25}H_{30}N_2O_4$: C, 71.07; H, 7.16; N, 6.63. Found: C, 70.98; H, 7.20; N, 6.63.

The second fraction (Rf 0.26, silica gel, heptane-ether, 1:1) was crystallized from heptane-petroleum ether, bp 30°–60° C to give 5.61 g (mp 83°–85° C, 41% yield) of 1,2-diphenyl-4-butyl-5-pivalyloxymethoxy-4-pyrazolin-3-one.

nmr (CDCl$_3$) δ 5.75 (—O—CH$_2$—OC).

Anal. Calcd for $C_{25}H_{30}N_2O_4$: C, 71.07; H, 7.16; N, 6.63. Found: C, 71.22; H, 7.25; N, 6.74.

EXAMPLE 5

1,2-DIPHENYL-4-BUTYL-5(4'-METHYLPHENYL-SULFONYLOXY)-4-PYRAZOLIN-3-ONE

First, the Thallium (I) salt of phenylbutazone was prepared. Thallium (I) ethoxide (2.24 g, 9 mmole) was dissolved in ether (100 ml) and allowed to react with 2.84 g (9.2 mmole) of phenylbutazone. The white suspension was stirred at room temperature for one hour then filtered and the residue was dried in a vacuum desiccator to give 4.55 g (mp 194°–202° C (dec.), 100% yield) of the Thallium (I) salt of phenylbutazone.

Anal. Calcd for $C_{19}H_{19}N_2O_2$ Tl: C, 44.59; H, 3.74. Found: 44.26; H, 3.93.

Then, p-Toluenesulfonyl chloride (0.95 g, 5.0 mmole) was allowed to react with a dimethylformamide (20 ml) suspension of the Thallium (I) salt of phenylbutazone. Within a few minutes the solvent became pink and a yellow solid, instead of the white Thallium (I) salt of phenylbutazone, was observed suspended in the pink solution. The suspension was stirred overnight in a tightly sealed flask, then it was diluted with 100 ml of ether and filtered. The filtrate was concentrated in vacuo to remove the ether and the dimethylformamide was evaporated under a stream of nitrogen. The residue from the evaporation was suspended in dichloromethane and filtered. Analysis of the filtrate by TLC showed that it contained only one major component. The dichloromethane was evaporated in vacuo and the residue was crystallized from ether to give 0.76 g (mp 112°–121° C, 33% yield) of yellow crystals which contained only one component by TLC analysis. Recrystallization of the yellow crystals gave analytically pure crystals, mp 125°–127° C with spectral properties identical to the crystals, mp 112°–121° C.

Anal. Calcd for $C_{26}H_{26}N_2O_4S$: C, 67.51; H, 5.66; N, 6.06. Found: C, 67.65; H, 5.74; N, 5.89.

EXAMPLE 6

1,2-DIPHENYL-4-BUTYL-5-ACETYLOXY-4-PYRAZOLIDIN-3-ONE

The title compound was prepared as in Example 1 except that the dichloromethane solution of the reaction product was extracted with the sodium bicarbonate solution only. The title compound was crystallized from dichloromethane-petroleum ether, bp 30°–60° C to give white crystals, mp 49°–51° C in 54% yield.

Anal. Calcd for $C_{21}H_{22}N_2O_3$: C, 71.97; H, 6.33; N, 7.99. Found: C, 71.79; N, 6.19; N, 8.16.

If the dichloromethane solution of the reaction product was not extracted with any base but crystallized from dichloromethanepetroleum ether bp 30°–60° C, 1,2-diphenyl-4-butyl-5-hydroxy-5-trifluoroacetyloxy-3-acetyloxy-3-pyrazoline was obtained in 70% yield as clear colorless crystals mp 63°–66° C.

Anal. Calcd for $C_{23}H_{23}N_2O_5F_3$: C, 59.47; H, 4.99; N, 6.03; F, 12.27. Found: C, 59.54; H, 5.02; N, 6.18; F, 12.24.

EXAMPLE 7

1,2-DIPHENYL-4-BUTYL-5-(N,N-DIMETHYLCARBAMOYLOXY)-4-PYRAZOLIDIN-3-ONE

An acetone (75 ml) solution of the potassium salt of phenylbutazone (2.34 g, 6.8 mmole) was allowed to react with 0.74 g (6.9 mmole) of N,N-dimethylcarbamoyl chloride at reflux for 48 hours. The acetone suspension was concentrated in vacuo and the residue was suspended in dichloromethane. The dichloromethane suspension was extracted twice with 20 ml of 0.1 N sodium hydroxide, then it was dried over sodium sulfate and concentrated in vacuo. The residue was crystallized from dichloromethane-hexane (3:50) to give 1.25 g (mp 136°–137.5° C, 48% yield) of the title compound.

Anal. Calcd for $C_{22}H_{25}N_3O_3$: C, 69.63; H, 6.44; N, 11.07. Found: C, 69.53; H, 6.41; N, 10.92.

EXAMPLE 8

1,2-DIPHENYL-4-BUTYL-5-PIVALYLOXY-4-PYRAZOLIDIN-3-ONE

First, the Thallium (I) salt was prepared in the same way as in Example 5, then 5.12 g (10 mmole) of the Thallium (I) salt of phenylbutazone was suspended in ether (100 ml) and allowed to react with 1.20 g (10 mmole) of pivalyl chloride. The suspension was stirred at room temperature for 6 hours, filtered and the filtrate was concentrated in vacuo. The residue was titrated with petroleum ether, bp 30°–60° C to give 2.95 g (mp 114°–115° C, 75% yield) of the title compound.

Anal. Calcd for $C_{24}H_{28}N_2O_3$: C, 73.44; H, 7.19; N, 7.14. Found: C, 73.40; H, 7.06; N, 7.18.

EXAMPLE 9

1,2-DIPHENYL-4-BUTYL-5-(N,N DIETHYLCARBAMOYLMETHOXY)-4-PYRAZOLIDIN-3-ONE and

1,2-DIPHENYL-4-BUTYL-4-(N,N-DIETHYLCARBAMOYLMETHYL)-3,5-PYRAZOLIDINEDIONE

N,N-Diethylchloroacetamide (3.00 g, 20 mmole) was added to an acetone (60 ml) solution containing 6.0 g (19.5 mmole) of phenylbutazone and 1.38 g (10 mmole) of potassium carbonate. The suspension was refluxed for 48 hours, then it was filtered, and the residue (1.20 g, 81% yield of potassium chloride) was washed with acetone (100 ml). The acetone filtrate was concentrated in vacuo, and the residue therefrom was titrated with dichloromethane. The dichloromethane suspension was filtered to give 1.16 g (17% yield) of the potassium salt of phenylbutazone as a white residue. The dichloromethane filtrate was concentrated in vacuo and the residue (7.30 g) was suspended in ether (50 ml). The ether suspension was filtered and the residue was washed with 20 ml of ether, then dried in a vacuum desiccator to give 3.50 g (mp 134°–135° C, 43% yield) of the C-alkylated product: nmr (CDCl₃) δ 3.1 S, 2,

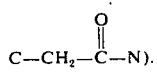

Anal. Calcd for $C_{25}H_{31}N_3O_3$: C, 71.23; H, 7.41; N, 9.97. Found: C, 71.14; H, 7.26; N, 10.00.

The ether filtrate was absorbed on silica gel and chromatographed on neutral silica gel (89 g) using ether as the eluent to give two fractions. The first fraction (Rf 0.33, silica gel, ether) was the C-alkylated product: 1.16 g, mp 129.5°–132° C, 13% yield. The second fraction (Rf 0.13, silica gel, ether) was the O-alkylated product: 2.25 g of a viscous oil, 22% yield. The O-alkylated was finally crystallized from dichloromethane-heptane, 10:60 to give 0.81 g (mp 80.5°–82° C, 10% yield) of white needles which had spectral properties identical with the crude viscous oil:

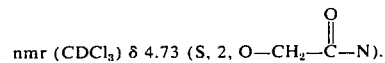

Anal. Calcd for $C_{25}H_{31}N_3O_3$: C, 71.23; H, 7.41; N, 9.97. Found: C, 71.15; H, 7.41; N, 9.82.

The preceding examples can be repeated with similar success by simply substituting the appropriate generically or specifically described reactants and/or operating conditions of this invention for those used in the preceding examples.

The pro-drug forms of this invention are suitably administered in oral dosage form, such as by tablet or capsule, by combining the same in a therapeutic amount with any oral pharmaceutically acceptable inert carrier, such as lactose, starch (pharmaceutical grade), dicalcium phosphate, calcium sulfate, Kaolin, mannitol and powdered sugar. In addition, when required, suitable binders, lubricants, disintegrating agents, and coloring agents can also be added. Typical binders include, without limitation, starch, gelatin, sugars such as sucrose, molasses, and lactose, natural and synthetic gums, such as acacia, sodium alginate, extract of Irish moss, carboxymethylcellulose, methylcellulose, and polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose and wood products, alginic acid, guar gum, citris pulp, carboxymethylcellulose, and sodium lauryl sulfate. Optionally, if desired, a conventionally, pharmaceutically acceptable dye can be incorporated into the oral dosage unit form, e.g., any of the standard FD&C dyes.

Any skilled artisan concerned with the subject matter of this invention can prepare these oral dosage forms by simply referring to the oral dosage form preparatory procedure outlined in "REMINGTON'S PHARMACEUTICAL SCIENCES," Fourteenth Edition (1970), pages 1659 through 1698 inclusive.

While the therapeutic dosage range for the compounds of this invention will vary with the size and needs of the patient, generally speaking, the daily dosage range, on an equivalent basis, will mimic that for phenylbutazone and oxyphenbutazone. See *Physicians' Desk Reference*, Twenty-eighth Edition (1974), pages 772–774.

From the foregoing description, one of ordinary skill in the art can easily ascertain the essential characteristics of this invention, and without departing from the spirit and scope thereof, can make various changes and modifications of the invention to adapt it to various usages and conditions. As such, such changes and modifications are properly, equitably, and intended to be, within the full range of equivalence of the following claims.

What we claim is:
1. A pro-drug compound of the formula:

(I) 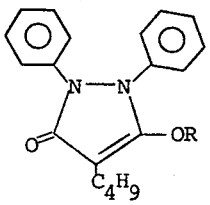

wherein R represents a member selected from the group consisting of a nicotinoyl group, an iso-nicotinoyl group, a picolinoyl group, an N-protected naturally occurring amino acid residue, wherein the protective group on the amino group of the amino acid residue is removable via hydrogenolysis or hydrolysis, and an amino acid residue containing a $C_1$–$C_2$ N,N-dialkylamino or a $C_4$–$C_6$ cycloalkylamino group.

2. The compound of claim 1:
1,2-Diphenyl-4-butyl-5-nicotinoyl-4-pyrazolin-3-one.
3. The compound of claim 1:
1,2-Diphenyl-4-butyl-5-picolinoyl-4-pyrazolin-3-one.
4. The compound of claim 1:
1,2-Diphenyl-4-butyl-5-iso-nicotinoyl-4-pyrazolin-3-one.
5. The compound of claim 1:
1,2-Diphenyl-4-butyl-5-pivalyloxy-4-pyrazolin-3-one.
6. The compound of claim 1:
1,2-Diphenyl-4-butyl-5-(N,N-dimethylcarbamoyloxy)-4-pyrazolin-3-one.
7. The compound of claim 1:
1,2-Diphenyl-4-butyl-5-(N,N-diethylcarbamoyloxy)-4-pyrazolin-3-one.
8. The compound of claim 1:
1,2-Diphenyl-4-butyl-5-(N-formylglycyloxy)-4-pyrazolin-3-one.
9. The compound of claim 1:
1,2-Diphenyl--butyl-5-(N-ethoxycarbonylglycyloxy)-4-pyrazolin-3-one.
10. The compound of claim 1:
1,2-Diphenyl-4-butyl-5-(N-benzyloxycarbonylglycyloxy)-4-pyrazolin-3-one.
11. The compound of claim 1:
1,2-Diphenyl-4-butyl-5-pivalyloxymethoxy-4-pyrazolin-3-one.
12. The compound of claim 1:
1,2-Diphenyl-4-butyl-5-benzoyloxymethoxy-4-pyrazolin-3-one.
13. The compound of claim 1:
1,2-Diphenyl-4-butyl-5-benzoyloxybenzyloxy-4-pyrazolin-3-one.
14. The compound of claim 1:
1,2-Diphenyl-4-butyl-5-acetyloxymethoxy-4-pyrazolin-3-one.
15. The compound of claim 1:
1,2-Diphenyl-4-butyl-5-(N,N-dimethylcarbamoylmethoxy)-4-pyrazolin-3-one.
16. The compound of claim 1:
1,2-Diphenyl-4-butyl-5-(N,N-diethylcarbamoylmethoxy)-4-pyrazolin-3-one.

* * * * *